United States Patent [19]

Kulpraghipanja

[11] Patent Number: 5,171,870
[45] Date of Patent: Dec. 15, 1992

[54] PROCESS FOR SEPARATING TRIGLYCERIDES HAVING DIFFERENT DEGREES OF UNSATURATION

[75] Inventor: Santi Kulpraghipanja, Inverness, Ill.

[73] Assignee: UOP, Des Plaines, Ill.

[21] Appl. No.: 688,751

[22] Filed: Apr. 22, 1991

[51] Int. Cl.$^5$ .............................................. C11B 7/00
[52] U.S. Cl. .................................. 554/193; 554/175; 554/191; 554/211
[58] Field of Search ..................... 260/428.5; 554/193, 554/191, 211, 175

[56] References Cited

U.S. PATENT DOCUMENTS

| | | | |
|---|---|---|---|
| 2,985,589 | 5/1961 | Broughton et al. | 210/34 |
| 3,040,777 | 4/1959 | Carson et al. | 137/625.15 |
| 3,328,439 | 6/1967 | Hamilton | 260/410.9 |
| 3,422,848 | 1/1969 | Liebman et al. | 137/625.15 |
| 3,706,812 | 12/1972 | De Rosset et al. | 260/674 SA |
| 4,048,205 | 9/1977 | Neuzil et al. | 260/428 |
| 4,275,081 | 6/1981 | Coleman et al. | 426/33 |
| 4,277,412 | 7/1981 | Logan | 260/428.5 |
| 4,284,580 | 8/1981 | Logan et al. | 260/428.5 |
| 4,353,838 | 10/1982 | Cleary et al. | 260/419 |
| 4,741,830 | 5/1988 | Hauck et al. | 210/635 |
| 4,770,819 | 9/1988 | Zinnen | 260/428.5 |
| 4,784,807 | 11/1988 | Zinnen | 260/428.5 |
| 4,793,921 | 12/1988 | Hauck et al. | 210/198.3 |
| 4,961,881 | 10/1990 | Ou | 260/428.5 |

FOREIGN PATENT DOCUMENTS 192797 of 1986 Japan.
214184 of 1988 Japan.

OTHER PUBLICATIONS

Plattner et al., Lipids, vol. 14, #2, 1979, pp.152-3.
Plattner et al., Journal of the American Oil Chemist, vol. 54, #11, 1977, pp.511-15.

Primary Examiner—Jose G. Dees
Assistant Examiner—Deborah D. Carr
Attorney, Agent, or Firm—Thomas K. McBride; John F. Spears, Jr.; Jack H. Hall

[57] ABSTRACT

The separation of unsaturated triglycerides on the basis of degree of unsaturation is achieved by an adsorptive chromatographic process in liquid phase with silane- or alcohol-treated silica gel as the adsorbent. Desorbents in the separation process include ketones, having from 3 to 8 carbon atoms, low molecular weight esters, having from 3 to 8 carbon atoms or p-cymene, or mixtures thereof, alone or mixed with a hydrocarbon diluent. The preferred temperature in the separation column is from 120°-150° C.

10 Claims, 2 Drawing Sheets

PROCESS FOR SEPARATING TRIGLYCERIDES HAVING DIFFERENT DEGREES OF UNSATURATION

FIELD OF THE INVENTION

The field of art to which this invention belongs is the solid bed adsorptive separation of triglycerides. More specifically, the invention relates to a process for separating triglyceride mixtures having at least two triglycerides with different degrees of unsaturation by a process which employs silica gel which has been chemically reacted with a treating agent.

BACKGROUND OF THE INVENTION

An economical and efficient method for separating triglycerides on the basis of degree of unsaturation has previously been sought to satisfy commercial pressures. For example, in Ou U.S. Pat. No. 4,961,881, the desirability of reducing the level of unsaturated fatty acid groups in synthetically produced triglycerides was disclosed since the product could be used as a cocoa butter extender. In view of more recent trends to reduce the monounsaturated components of triglyceride mixtures for health reasons, the applications of such a process in edible products, such as margarine, mayonnaise, etc., are apparent.

Thus, the value of available feed materials such as soybean oil, cottonseed oil, linseed oil, corn oil, peanut oil, sunflower oil, safflower oil, canola oil, olive oil, rich bran oil, sesame, and almond, etc., can be enhanced by processing to give fractions which are enriched or deleted in unsaturation. Other highly saturated feeds, such as tallow, lard, coconut, palm oil, etc., may be reacted with unsaturated fatty acids via an interesterification process, as disclosed in U.S. Pat. Nos. 4,275,081 or 3,328,439, to increase the degree of unsaturation and the product thereof can be separated by the process of the invention.

The separation of many classes of compounds by selective adsorption on molecular sieves or zeolites as well as other adsorbents is well known. Also, various separations based on the degree of unsaturation are known, e.g., esters of saturated fatty acids from unsaturated fatty acids with X or Y zeolites exchanged with a selected cation, from U.S. Pat. No. 4,048,205, monoethanoid fatty acids from diethanoid fatty acids with cross-linked polystyrenes, e.g., "Amberlite", from U.S. Pat. No. 4,353,838. A process for separating a mixture of triglycerides, based on the iodine values, is shown in U.S. Pat. Nos. 4,277,412 and 4,284,580 in which permutite and surface-aluminated silica gel adsorbents, respectively, can be used. However, both of these require silver-exchanged surface-aluminated silica gel adsorbents, which is not only undesirable in food product preparation, but rapid fouling of these adsorbents by any impurities in the feed mixtures has limited commercial application of these materials. The adsorbents of the invention are not subject to the limitation of these prior art materials. Ou U.S. Pat. No. 4,961,881 describes a process for overcoming the deactivation of the surface-treated silica gel of 4,284,580 by continuously or intermittently regenerating the adsorbent with hydrogen peroxide or an organic peroxide. The improved adsorbents of the present invention are remarkably stable and thus do not exhibit the rapid deactivation that is exhibited by the prior art absorbents.

The adsorption properties of silane- and/or alcohol-treated silica gels have been reported and found useful in certain analytical separations, e.g., thin layer chromatography (TLC). For example, Plattner et al, Lipids 14 (2), (1979), pp 152-3 reported that triglycerols could be separated by both chain length and number of double bonds with reverse phase columns, i.e., $\mu$-Bondapak $C_{18}$ or $\mu$-Porasil silica gels with octadecyl silyl groups bonded to silica particles. Also, Plattner et al, JAOCS 54 (11) (November 1977) pp 511-15. Acetonitrile: acetone (2:1 v/v) mixtures were used as elution agents. Neither, however, describes a process capable of separating triglycerides by degree of unsaturation in bulk quantities nor the preferred desorbents of the present invention.

A process for making surface-silanized TLC separation materials for use in aqueous elution agent systems is disclosed in U.S. Pat. Nos. 4,741,830 and 4,793,921, incorporated by reference herein.

Japanese Public Disclosure No. 192797/86 discloses a method for concentrating eicosapentaenoic acid and docosahexaenoic acid in their triglyceride forms with silica gel chemically bound with an octadecyl group or a styrene-divinylbenzene copolymer.

Zinnen U.S. Pat. No. 4,784,807 discloses the separation of triglycerides based on degree of unsaturation with omega zeolite or carbon adsorbents and ketones, toluene and ketone/aliphatic hydrocarbon mixtures as desorbents.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system, which are also known, e.g., by rotary disc valves showing in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The functions and properties of adsorbents and desorbents in the chromatographic separation of liquid components are well known, but for reference thereto, Zinnen et al U.S. Pat. No. 4,770,819, which relates to the separation of diglycerides from triglycerides with omega zeolite or silica adsorbents is incorporated herein. From FIG. 1 and Example II of this patent, it can be seen that Zinnen et al was not able to separate triglycerides on the basis of degree of unsaturation with silica gel, since all the triglycerides eluted at the same time.

I have found adsorbents, which, in combination with certain desorbent liquids, will selectively adsorb the more highly unsaturated triglycerides contained in triglyceride mixtures having components with different degrees of unsaturation. The more saturated (less unsaturated) triglycerides are relatively non-adsorbed and elute first. Thus, the more saturated triglyceride components of the feed are eluted as raffinate and the more highly unsaturated triglycerides are adsorbed and eluted as extract by desorption with the desorbent.

These adsorbents are thermally stable and thus can be regenerated easily at elevated temperatures without collapsing the pore structure. Furthermore, since there are no metal exchange ions, they are deemed suitable for the separation of food products and are chemically stable to impurities contained in the feed.

I have discovered a method for separating mixtures of unsaturated triglycerides on the basis of degree of unsaturation. The triglycerides may include monounsaturated and polyunsaturated triglycerides.

SUMMARY OF THE INVENTION

The present invention is a process for separating feed mixtures of triglycerides having different degrees of saturation into fractions containing higher degrees of unsaturation and lower degrees of unsaturation, for example, monounsaturated triglycerides can be separated and recovered from a mixture of monounsaturated and polyunsaturated triglycerides. The process comprises contacting the mixture at adsorption conditions with an adsorbent comprising silica gel which has been treated with a silane or an alcohol. The treatment results in a surface-modified hydrophobic silica gel that is capable of selectively adsorbing the triglycerides having higher degrees of unsaturation. The diunsaturated triglycerides and other polyunsaturated triglycerides are more selectively adsorbed than monounsaturated triglycerides. The polyunsaturated triglycerides are desorbed by a liquid ketone having from 3 to 8 carbon atoms or a mixture thereof with a normal alkane. Monounsaturated triglycerides are relatively unadsorbed by the molecular sieve and are removed before the polyunsaturated triglycerides and, together with desorbent, constitute the raffinate. The desorbent may be selected from ketones having up to 8 carbons, e.g., acetone, methyl ethyl ketone, the pentanones, hexanones, heptanones and octanones, esters, e.g., ethyl acetate, and alkyl substituted benzenes, such as p-cymene. Specific examples of ketones useful in the process are acetone, methyl ethyl ketone, diethyl ketone, methyl propyl ketone, 2-hexanone, 2-heptanone, 3-heptanone, 2-octanone, etc., and mixtures thereof with hydrocarbons. The desorbent may be diluted with a hydrocarbon, e.g., a normal alkane, to modify the strength of the desorbent. Desorbent materials, such as n-hexane, p-cymene and 2-heptanone, which are GRAS-listed, and therefore approved for processing foods, are preferred.

The invention, more particularly, is a process for separating triglycerides having different degrees of unsaturation comprising contacting a mixture of triglycerides having different degrees of unsaturation with a silica gel adsorbent to selectively adsorb the more highly unsaturated triglycerides, removing said triglycerides having lower degrees of unsaturation from said adsorbent and desorbing said triglycerides with higher degrees of unsaturation from said adsorbent with a desorbent comprising from about 3% (vol.) up to about 25% (vol.) of a ketone having from 3–8 carbon atoms, p-cymene or a low molecular weight ester diluted with a normal alkane, wherein said silica gel has been treated with an agent selected from the group consisting of silanes and alcohols. In a more specific embodiment, the separation is conducted a temperature of at least about 100° C., preferably from about 120° C. to about 150° C.

In a specific embodiment, a feed composition analyzing from 40 to 92% polyunsaturated triglycerides can be separated by the process of the invention to produce a product stream with an increase of at least about 4 percentage points, to, e.g., up to about 96% polyunsaturated triglycerides or higher.

Other embodiments of my invention encompass details about feed mixtures, adsorbents, desorbent materials and operating conditions, all of which are hereinafter disclosed in the following discussion of each of the facets of the present invention.

DETAILED DESCRIPTION OF THE INVENTION

Figure 1:
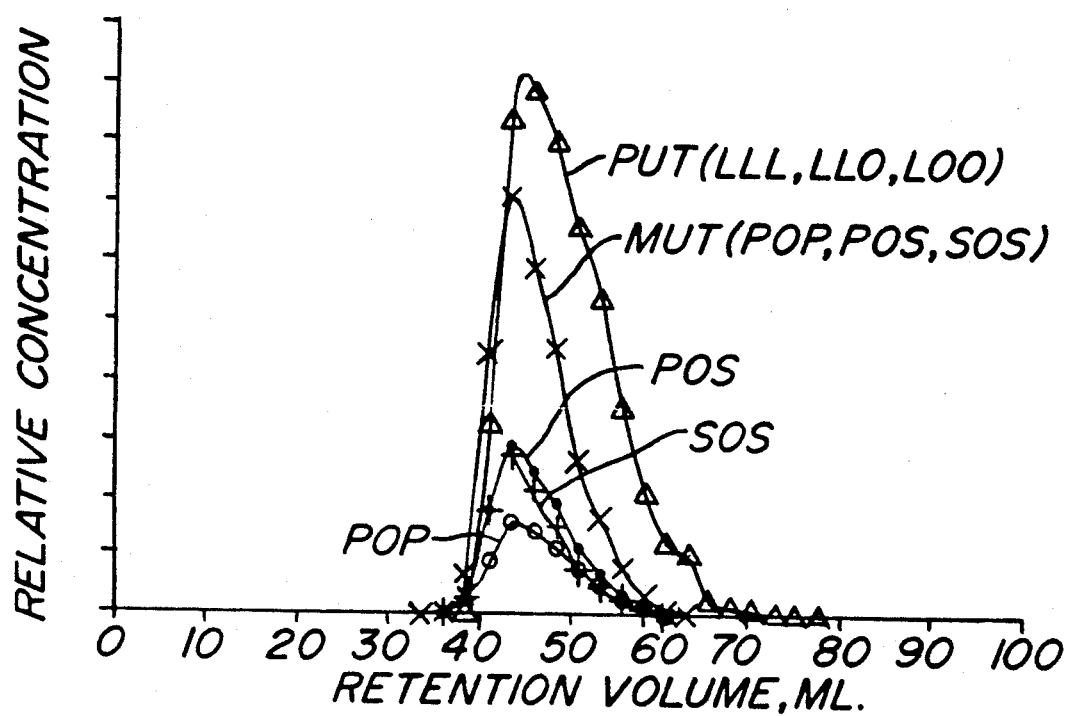
FIG. 1 is a graphic representation of a chromatographic separation of polyunsaturated triglycerides from monounsaturated triglycerides with a silane treated silica gel adsorbent and 10/90 (wt./wt.) mixture of acetone and isooctanes as desorbent.

Highly unsaturated triglycerides are desirable fats and oils for use in certain foods, such as mayonnaise, salad dressings, etc. Many natural or synthetic products contain high percentages of polyunsaturated triglycerides along with substantial amounts of monounsaturated and saturated triglycerides. It would be commercially desirable to remove some (or all) of the saturated and monounsaturated triglycerides (PUT's) while increasing the concentration of polyunsaturated triglycerides (PUT's) to at least about 96% by means of a direct separation. It has been proposed to separate triglycerides as a class from free fatty acids, but in order to obtain highly unsaturated triglycerides it was necessary to first subject the natural triglyceride feeds to an interesterification reaction step to interchange unsaturated free fatty acids with saturated fatty acid groups of the triglyceride molecule. Such extra step is costly and can be avoided by the separation process of the present invention.

Feed materials which may be used in the separation include naturally occurring oils, such as linseed oil, cottonseed oil, corn oil, peanut oil, palm oil, sunflower oil, canola oil, safflower oil, etc. The preferred feed material will have a polyunsaturated triglyceride content of 75 to 92%, which can be upgraded by the process of the invention to 96% or higher polyunsaturated triglycerides.

The adsorbents used in the invention are silane- or alcohol-treated silica gels. The treated silica gels can be obtained from silica gels by reaction with a silane or an alcohol. For example, surface-modified silica gel separation materials made by the general chemical reaction disclosed in U.S. Pat. No. 4,793,921 can be used. I prefer to use unsupported silica gel having the following characteristics as the starting material:

| Particle size: | 35 to 60 Mesh (U.S.) |
| --- | --- |
| Pore size: | 20 to 150Å |
| Pore volume: | .45 to 1.2 cc/g |
| Surface area (BET): | 300 to 800 m$^2$/g |

I then treat the silica gel at about 50° C. with a mixture of methyl trichlorosilane and isooctane for 2 hours followed by washing and drying. Various amounts of the silane can be incorporated into the silica by reaction with the surface silicon units, that is, from about 0.5% (wt.) to about 20% (wt.), preferably from about 10% (wt.) to about 15% (wt.).

An esterified silica gel, made by treating silica gel with an alcohol, is also useful in the invention. The alcohol may contain from 1 to 8 carbon atoms and includes methanol, ethanol, propanol, isopropanol, butanol, pentanol, etc. To prepare the esterified silica gel, the silica gel is dried at 175° C. under $N_2$ and then esterified with ethanol at 200° C. for 3 hours in a Parr bomb.

The water content of the adsorbent affects the separation capacity and exchange rates and may also affect its stability. Acceptable levels of water in the adsorbent in terms of loss on ignition (LOI) are from 0 to 10% (wt.), preferably from 0-3% (wt.). To reduce water content to the desired level, the adsorbent may also be dried in air, nitrogen, or other gas at elevated temperature. The adsorbent may also be dried by application of vacuum, maintaining the temperature initially at room temperature until most of the water is removed, then raising the temperature to 50° C. while maintaining vacuum.

The general scheme for the adsorption separation such as practiced here is known from, e.g., Broughton, U.S. Pat. No. 3,985,589. Briefly, the less adsorbed feed component(s) is eluted from the non-selective void volume and weakly adsorbing volume before the more strongly adsorbed component(s). The relatively unadsorbed component(s) is thereby recovered in the raffinate stream, while the more strongly adsorbed component(s) is recovered in the extract stream.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor phase operation. Adsorption conditions will include a temperature range of from about 60° C. to about 200° C., preferably from about 120° C. to about 150° C., and a pressure sufficient to maintain liquid-phase, ranging from about atmospheric to about 400 psig, with from about atmospheric to about 200 psig usually being adequate. Desorption conditions will include the same range of temperatures and pressures as used for adsorption conditions.

At lower temperatures, e.g., about 60° C., although separation takes place, a significant amount of PUT's "break through" with the non-adsorbed components of the feed mixture (MUT's) near the void volume, significantly lowering the recovery of PUT's. In some cases, part of the MUT's are eluted at some later time, prior to elution of the PUT's, thereby reducing the purity of the product PUT's. It is theorized that because of the slow transfer rate of PUT's at the lower temperature some of the PUT's are unable to enter the pores of the adsorbent and, hence, are removed from the void volume with the non-adsorbed species. It was found that the "breakthrough" could be reduced or eliminated by raising the temperature of the column, leading to the theory that the separation was improved by increasing the mass transfer rate. For the above reasons, it is desirable and advantageous to operate the separation column at temperatures of at least about 100° C. and preferably, between 120° C. and 150° C.

At least a portion of the raffinate stream, which contains the concentrated mixed triglycerides product, and preferably at least a portion of the extract stream from the separation process are passed to separation means, typically fractionators or evaporators, where at least a portion of desorbent material is separated to produce a raffinate product and an extract product, respectively.

The desorbent material for the preferred isothermal, isobaric, liquid-phase operation of the process of my invention comprises a low molecular weight ketone having from 3-8 carbon atoms, p-cymene or a low molecular weight ester having from 3 to 8 carbon atoms. The ketones include acetone, methyl ethyl ketone, diethyl ketone, methyl butyl ketone, 2-heptanone, 3-heptanone, dipropyl ketone, 2-octanone, 3-octanone, etc. Mixtures of the ketones with hydrocarbon liquids, e.g., paraffinic liquids, are useful as desorbents because of their ability to modify the strength of the desorbent. The esters include methyl acetate, ethyl acetate, methyl butyrate, ethyl butyrate, methyl amylate, ethyl amylate, etc. Mixtures of esters with hydrocarbon liquids, e.g., paraffinic liquids may also be used. The hydrocarbon liquid functions as a diluent to modify the strength of the desorbent.

A dynamic testing apparatus is employed to test various adsorbents with a particular feed mixture and desorbent material to measure the adsorption characteristics of retention, capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively, or determine quantitatively, one or more components in the effluent stream leaving the adsorbent chamber. A pulse test, performed using this apparatus and the following general procedure, is used to determine data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer or of a raffinate component, or both, and of a particular extract component, all diluted in desorbent material is injected for a duration of several minutes. Desorbent material flow is resumed, and the tracer or the raffinate component (or both) and the extract component are eluted as in a liquid-solid chromatographic operation. The effluent can be analyzed onstream, or, alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, the rate of desorption of an extract component from the adsorbent and selectivity. The retention volume of an extract or a raffinate component may be characterized by the distance between the center of the peak envelope of the extract or raffinate component and the center of the peak envelope of the tracer component (void volume) or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. The narrower the peak width, the faster the desorption rate. Selectivity, $\beta$, is determined by the ratio of the net retention volumes of the more strongly adsorbed component to each of the other components.

The examples shown below are intended to further illustrate the process of this invention without unduly limiting the scope and spirit of said process. In the examples, the fatty acid residues are sometimes abbreviated as follows: P=palmitoyl, S=stearyl, O=oleyl and L=linoleyl. Also, a void volume of 41.0 ml, previously determined experimentally for similar adsorbents, was assumed and used as the reference point for calculating net retention volume.

EXAMPLE I

A pulse test as described above was performed to evaluate the process of the present invention for separating triglycerides of several degree of unsaturation. The column was filled with 70 cc of silanized silica gel adsorbent and maintained at a temperature of 150° C. and a pressure sufficient to provide liquid-phase operations. The adsorbent was prepared by equilibrating 100 g of silica gel (Davisil 636 available from Davison Division of W. R. Grace and Co.) with a mixture of 10 g of methyl trichlorosilane and 200 ml isooctane for 2 hours at 50° C. Then, the adsorbent was washed two times with isooctane and finally, dried at 60° C. overnight. The feed was 5 cc of a mixture of three triglycerides, each having a different degree of unsaturation and was prepared by the reaction, at 70° C., of stearic acid and triolein in the presence of an enzyme, Rhizopus japonicus, immobilized on an alumina support to produce SOS, OOO AND SOO. The triglyceride reaction mixture was mixed with 90% (wt.) n-hexane. The enzyme-catalyzed interesterification is well known. Japanese Kokai No. 214,184/88.

The desorbent was 7% 2-heptanone in n-hexane. The desorbent material was run continuously at a nominal liquid hourly space velocity (LHSV) of 1 (1.28 ml per minute flow rate). At some convenient time, the desorbent was stopped and 5 cc of the feed mixture was injected at a rate of 1.28 ml/min. The desorbent stream was then resumed at 1 LHSV and continued to pass into the adsorbent column until all of the feed components had been eluted from the column as determined by analyzing the effluent stream leaving the adsorbent column. The monounsaturated distearyl oleyl glyceride (SOS) was least strongly adsorbed and will be more concentrated in the initial eluent than in the feed, followed by the diunsaturated triglyceride (stearyl dioleyl triglyceride (SOO)). Triunsaturated triglyceride (OOO), the most strongly adsorbed component, was desorbed and eluted last. The results are set forth in the following Table 1 of gross retention volumes (GRV), net retention volumes (NRV), selectivities ($\beta$) and width at one-half peak height (HW). The results show a low level of selectivity, but the capability of concentrating each of the feed components.

TABLE 1

| Component | GRV | NRV | Selectivity ($\beta$) | HW |
|---|---|---|---|---|
| Void Volume | 41.0 | 0 | $\infty$ | — |
| SOS | 59.7 | 18.7 | 1.1 | 6.77 |
| OOO | 61.8 | 20.8 | 1.0 | 5.28 |
| SOO | 60.7 | 19.7 | 1.1 | 5.43 |

EXAMPLE II

The pulse test of Example I was repeated, except that the adsorbent was a silica gel treated with ethanol in the following manner: 100 parts (wt.) of silica gel (Davison 636) was dried at 175° C. under nitrogen and reacted with 160 ml ethanol in a Parr bomb at 200° C. for 3 hours. The feed was a mixture of 8% (wt.) cocoa butter (mixture of MUT's) and 10% (wt.) safflower oil (mixture of PUT's) in n-hexane. The desorbent was a 10/90 mixture of 2-heptanone/n-hexane. The temperature in the column was 150° C. and flow rate was 1.26 ml/min and a pressure of 240 psi to maintain liquid phase. As seen in the following Table 2 of results, the MUT's are eluted first followed by the PUT's. The individual MUT's were annalyzed and listed in the table.

TABLE 2

| Component | GRV | NRV | Selectivity ($\beta$) | HW |
|---|---|---|---|---|
| Void Volume | 41.0 | 0 | $\infty$ | — |
| MUT's (POP, POS, SOS) | 57.2 | 16.2 | 1.5 | 10.4 |
| POP | 59.8 | 18.8 | 1.3 | 10.0 |
| POS | 57.8 | 16.8 | 1.4 | 11.3 |
| SOS | 53.6 | 12.6 | 1.9 | 17.4 |
| PUT's (LLL, LLO, LOO) | 65.1 | 24.1 | 1.00 | 7.7 |

Two further pulse tests were run under the same conditions with the same feed and adsorbent, but with an 80/20 and 60/40 mixture of p-cymene/n-hexane, respectively. Thee results are shown in the following Tables 3 and 4.

TABLE 3

| Component | GRV | NRV | Selectivity ($\beta$) | HW |
|---|---|---|---|---|
| Void Volume | 41.0 | 0 | $\infty$ | — |
| MUT's (POP, POS, SOS) | 58.5 | 17.5 | 1.6 | 8.64 |
| POP | 60.9 | 19.9 | 1.4 | 11.71 |
| POS | 58.5 | 17.5 | 1.6 | 8.49 |
| SOS | 57.4 | 16.4 | 1.7 | 7.56 |
| PUT's (LLL, LLO, LOO) | 69.2 | 28.2 | 1.00 | 22.31 |

TABLE 4

| Component | GRV | NRV | Selectivity ($\beta$) | HW |
|---|---|---|---|---|
| Void Volume | 41.0 | 0 | $\infty$ | — |
| MUT's (POP, POS, SOS) | 64.9 | 13.9 | 1.73 | 12.4 |
| POP | 68.4 | 17.4 | 1.38 | 17.6 |
| POS | 64.9 | 13.9 | 1.73 | 12.1 |
| SOS | 63.5 | 12.5 | 1.93 | 10.5 |
| PUT's (LLL, LLO, LOO) | 85.1 | 24.1 | 1.00 | 37.4 |

EXAMPLE III

Two further pulse tests were run in which the monounssaturated triglyceride components (MUT's) of the feed were separated from the polyunsaturated triglyceride components (PUT's) as a group, using a silanized silica gel adsorbent analyzing 10% trichloromethyl silane (TCMS). In the first pulse test, ethyl acetate (5% in n-hexane) was the desorbent; in the second pulse test the desorbent was 80% p-cymene in n-hexane. The silanized silica gel was prepared in the same manner as Example I except that 14 parts (wt.) of TCMS) was added slowly to the silica gel (Davison 636) over a 20 minute period while heating the sample. The sample was purged with air at ambient temperature overnight. The feed was 5 cc of a mixture of 8% cocoa butter (MUT's), 10% safflower oil (PUT's)) and 82% 2-pentane. The temperature in the first pulse test was 60° C. and the flow rate was 1.23 ml/min. In the second pulse test the temperature was 150° C. and the flow rate was 1.21 ml/min. MUT's were separated from PUT's as shown in the following results in Tables 5 and 6.

TABLE 5

| Component | GRV | NRV | Selectivity (β) |
|---|---|---|---|
| Void Volume | 41.0 | 0 | ∞ |
| MUT's (POP, POS, SOS) | 64.7 | 23.7 | 1.6 |
| POP | 73.3 | 32.3 | 1.2 |
| POS | 65.0 | 24.0 | 1.6 |
| SOS | 63.7 | 22.7 | 1.7 |
| PUT's (LLL, LLO, LOO) | 78.8 | 37.8 | Ref. |

TABLE 6

| Component | GRV | NRV | Selectivity (β) | HW |
|---|---|---|---|---|
| Void Volume | 41.0 | 0 | ∞ | — |
| MUT's (POP, POS, SOS) | 57.6 | 16.6 | 1.4 | 7.78 |
| POP | 58.8 | 17.8 | 1.3 | 9.27 |
| POS | 57.6 | 16.6 | 1.3 | 7.81 |
| SOS | 56.8 | 15.8 | 1.4 | 6.70 |
| PUT's (LLL, LLO, LOO) | 63.3 | 22.2 | 1.0 | 16.52 |

EXAMPLE IV

The pulse test of Example III was repeated except that the adsorbent was obtained by reacting 100 g silica gel with 20 g TCMS (in 5% solution in ethanol), the temperature in the pulse test column was 60° C. and the desorbent was a 10/90 (vol.) mixture of acetone and isooctane. The feed was 5 ml of a mixture of 8% cocoa butter (MUT's) and 10% safflower oil (PUT's) in 82% (wt.) isooctane. The results are shown in FIG. 1, in which relative concentration of each component is plotted against time, i.e., the volume of desorbent introduced into the column, and in the following Table 7.

TABLE 7

| Component | GRV | NRV | Selectivity (β) |
|---|---|---|---|
| Void Volume | 41.0 | 0 | ∞ |
| MUT's (POP, POS, SOS) | 45.5 | 4.5 | 1.7 |
| POP | 46.0 | 5.0 | 1.5 |
| POS | 45.6 | 4.6 | 1.6 |
| SOS | 45.0 | 4.0 | 1.9 |
| PUT's (LLL, LLO, LOO) | 48.5 | 7.5 | 1.00 |

EXAMPLE V

Figure 2:
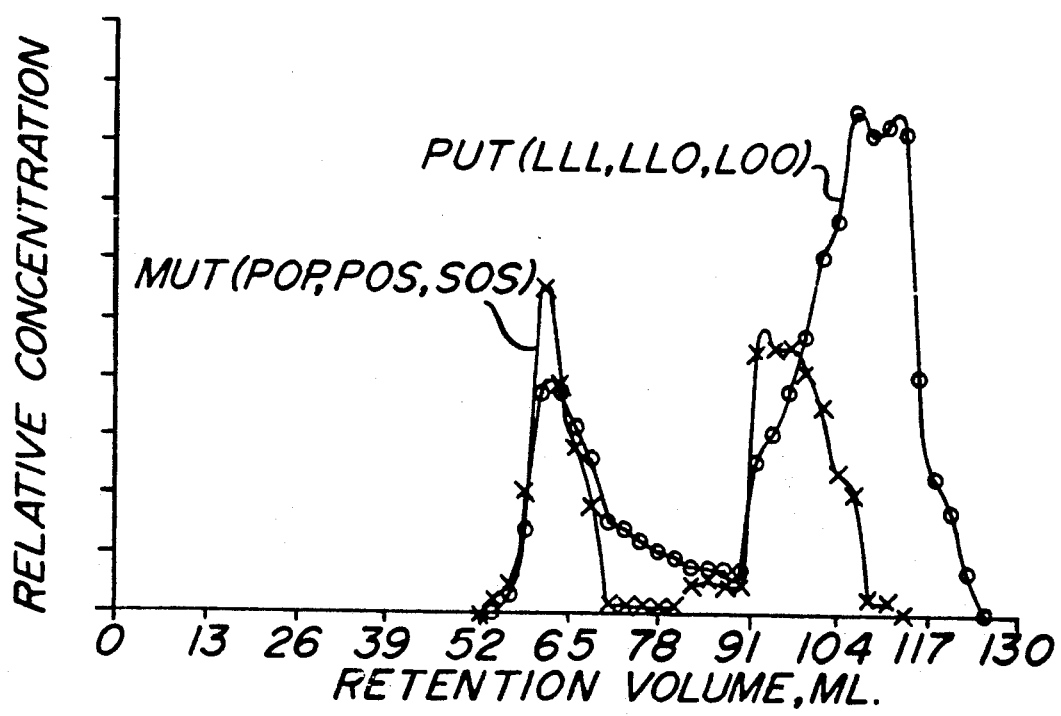
FIG. 2 is similar to FIG. 1 except that the desorbent is a 3% (wt.) solution of acetone in n-hexane.
Figure 3:
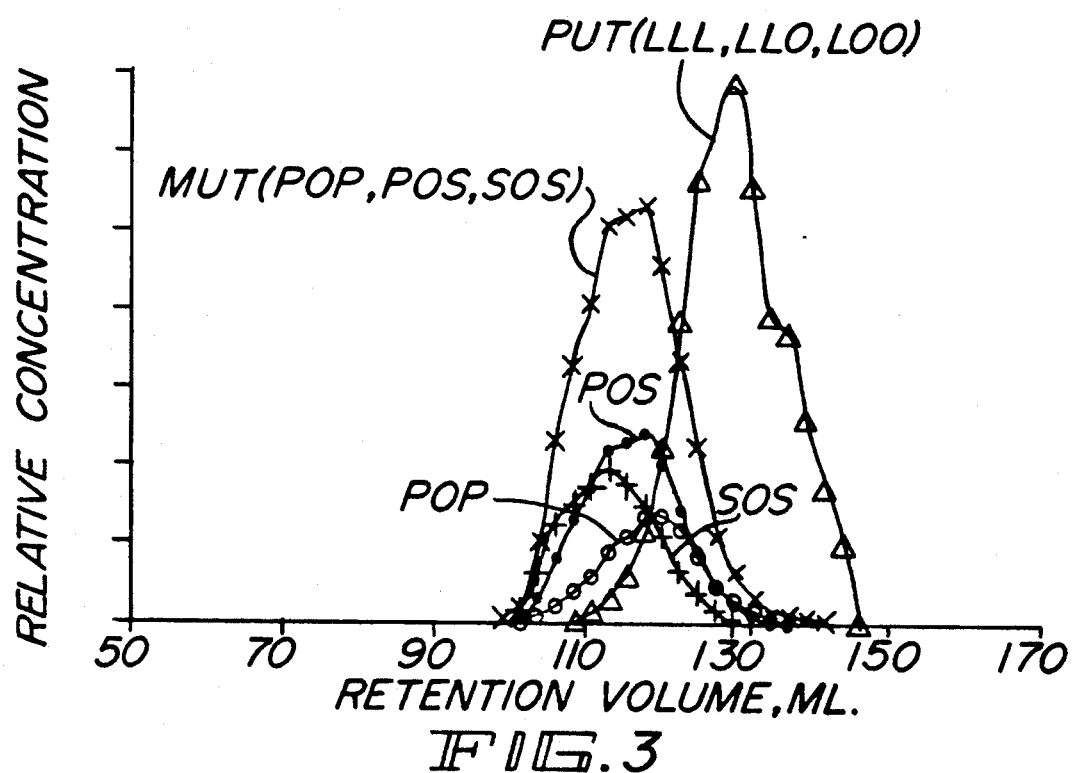
FIG. 3 is similar to FIG. 2 except that the temperature of the column is increased to 120° C.

Two further pulse tests were run on an MUT/PUT feed mixture of 8% cocoa butter and 10% safflower oil in n-hexane. The adsorbent was obtained by reacting 100 g silica gel (Davison 636) with 14 g TCMS added slowly while heating over about a 20-minute period. the sample was purged with air overnight washed with acetone/water and finally, dried overnight at 60° C. The desorbent was 3% acetone in n-pentane. The column temperature was 60° in the first pulse test and 120° C. in the second. The flow rate in both tests was 1.18 ml/min. At the lower temperature, a breakthrough of both PUT and MUT components is observed at about 64 ml (GRV) which can be eliminated by increasing the operating temperature of the separation to 120° C., as seen in FIGS. 2 and 3, in which the relative concentration of each component is plotted against the volume of desorbent introduced into the column of the first and second pulse tests, respectively. Thus, the yield (% recovery) of PUT's is greatly increased at higher temperatures. The results of the two pulse tests are further shown in the following Tables 8 and 9, respectively.

TABLE 8

| Component | GRV | NRV | Selectivity (β) |
|---|---|---|---|
| Void Volume | 41.0 | 0 | ∞ |
| MUT's (POP, POS, SOS) | 96.5 | 55.5 | 1.18 |
| PUT's (LLL, LLO, LOO) | 106.7 | 65.7 | 1.00 |

TABLE 9

| Component | GRV | NRV | Selectivity (β) |
|---|---|---|---|
| Void Volume | 41.0 | 0 | ∞ |
| MUT's (POP, POS, SOS) | 115.6 | 74.6 | 1.2 |
| POP | 118.9 | 77.9 | 1.1 |
| POS | 115.9 | 74.9 | 1.2 |
| SOS | 113.1 | 72.1 | 1.2 |
| PUT's (LLL, LLO, LOO) | 129.8 | 88.8 | 1.00 |

What is claimed is:

1. In a continuous process for separating monounsaturated triglycerides from polyunsaturated triglycerides comprising contacting a mixture of mono- and polyunsaturated triglycerides with a silica gel adsorbent to selectively adsorb said polyunsaturated triglycerides, removing said monounsaturated triglycerides from said adsorbent and desorbing said polyunsaturated triglycerides from said adsorbent with a desorbent comprising up to about 25% (vol.) of a ketone having from 3-8 carbon atoms, p-cymene or a low molecular weight ester, said adsorbent comprising a silica gel which has been treated with an alcohol.

2. The process of claim 1 wherein said separation is conducted at a temperature of at least about 100° C.

3. The process of claim 2 wherein said temperature is from about 120° C. to about 150° C.

4. The process of claim 1 wherein said alcohol is methanol.

5. The process of claim 1 wherein said alcohol is ethanol.

6. The process of claim 1 wherein said desorbent is a ketone having from 3 to 8 carbon atoms.

7. The process of claim 6 wherein said desorbent is 2-heptanone.

8. The process of claim 6 wherein the concentration of said ketone in the desorbent is from 3 to 20% (vol.).

9. The process of claim 8 wherein said ketone is diluted with n-hexane.

10. The process of claim 1 wherein said desorbent comprises p-cymene.

* * * * *